United States Patent [19]

Miller et al.

[11] Patent Number: 4,480,894
[45] Date of Patent: Nov. 6, 1984

[54] CURTAIN FOR SHROUDING WELDING OPERATIONS

[75] Inventors: Charles G. Miller, Pasadena; James B. Stephens, La Crescenta, both of Calif.

[73] Assignee: Wilson Sales Co., Inc., South El Monte, Calif.

[21] Appl. No.: 516,290

[22] Filed: Jul. 22, 1983

Related U.S. Application Data

[60] Division of Ser. No. 341,004, Jan. 20, 1982, Pat. No. 4,408,834, which is a division of Ser. No. 201,052, Oct. 27, 1980, Pat. No. 4,330,177, which is a continuation of Ser. No. 946,163, Sep. 27, 1978, abandoned.

[51] Int. Cl.³ .............................................. G02B 27/02
[52] U.S. Cl. ..................................... 350/167; 160/351; 350/276 R
[58] Field of Search ................... 350/276 R, 319, 321, 350/167; 160/351

[56] References Cited

U.S. PATENT DOCUMENTS 1,648,977 11/1927 Weidner ................................. 40/615
3,477,492 11/1969 Suess ................................... 160/351
3,718,078 2/1973 Plummer ............................. 350/129

Primary Examiner—Bruce Y. Arnold
Attorney, Agent, or Firm—Donald D. Mon; David O'Reilly

[57] ABSTRACT

A curtain for surrounding welding and cutting operations, especially electric arc welding and electric arc cutting operations to protect the eyes of otherwise unprotected observers such as supervisors, adjacent workers, and visitors to the welding operation. The curtain contains dyes for the purpose of absorbing radiation of wavelengths of potential hazard to such eyes. Because no dye can absorb all potentially harmful radiation and still provide some visibility, means is provided to improve the protection by means of reducing the exposure of the retina to undesirable intensities by optically enlarging the small arc spot, and by presenting the eye with general area illumination instead of pinpoint illumination.

5 Claims, 8 Drawing Figures

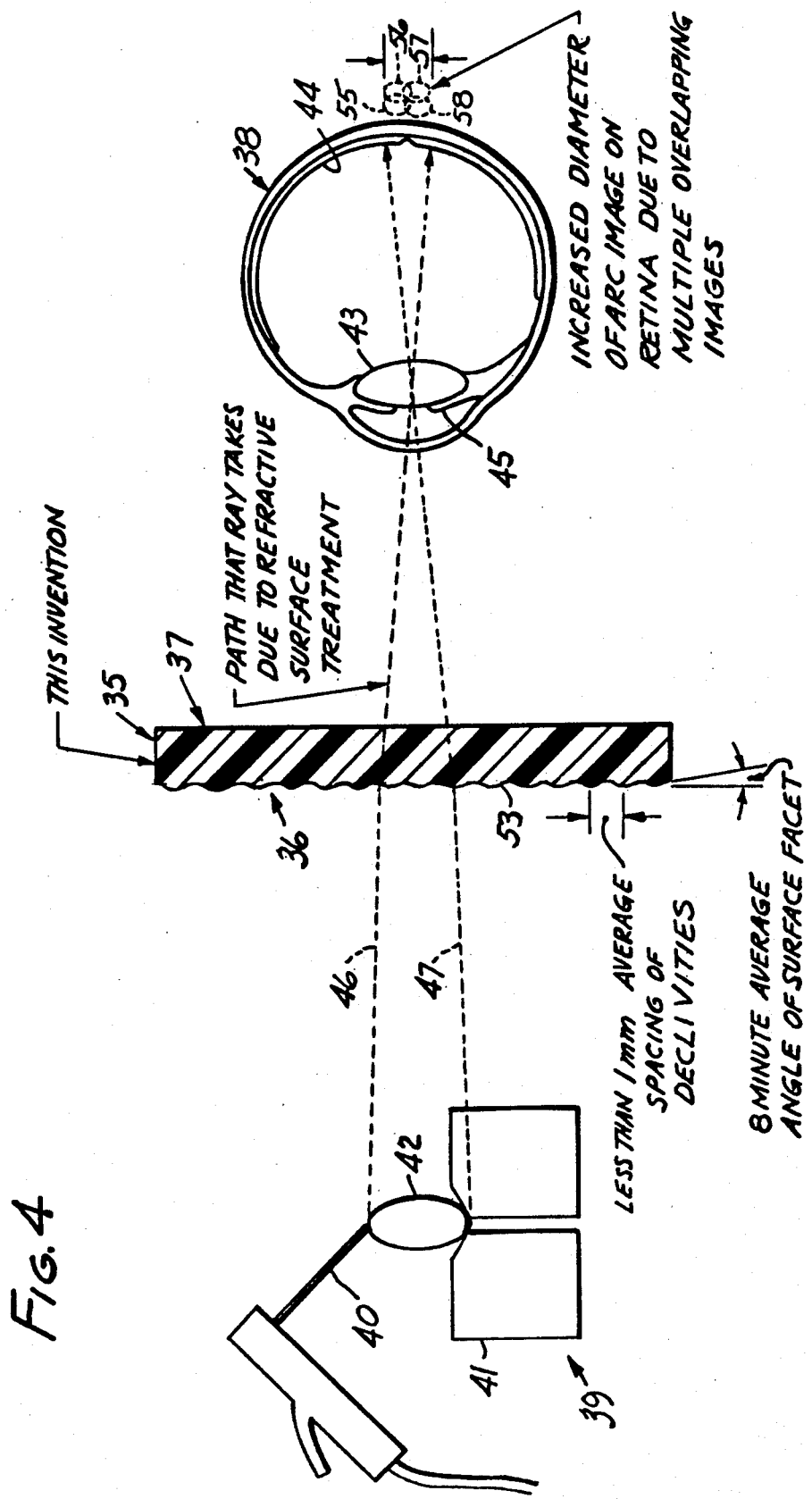

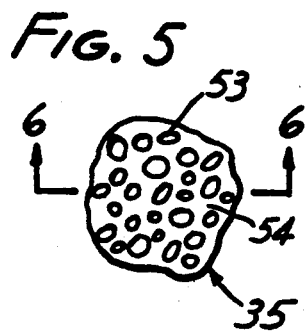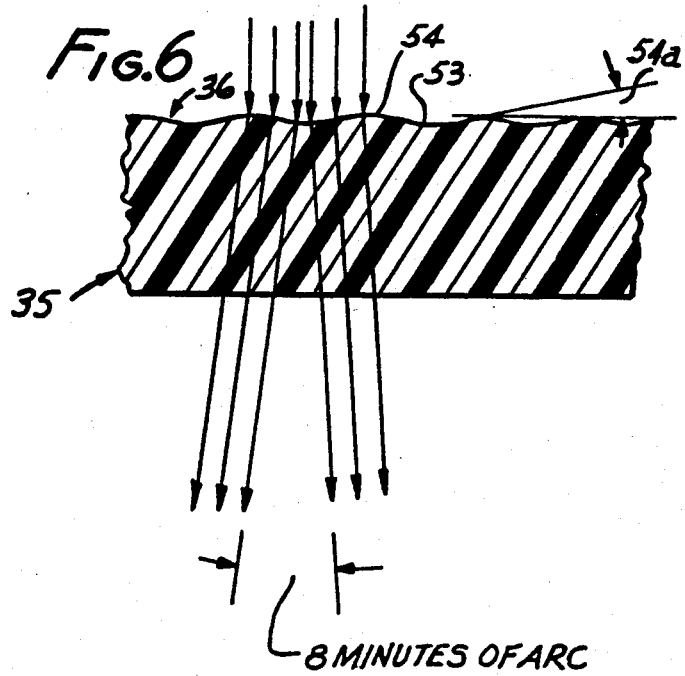

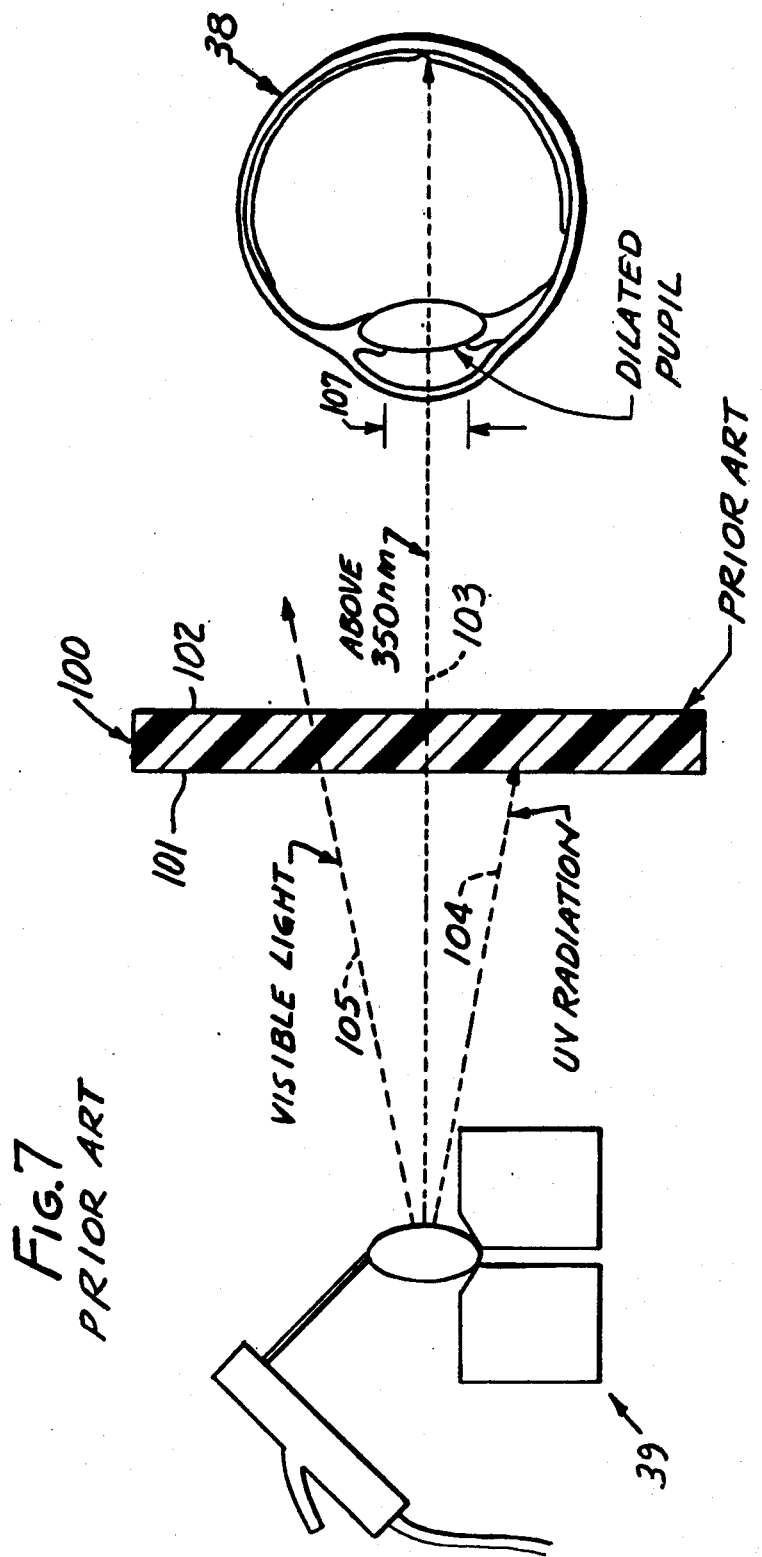

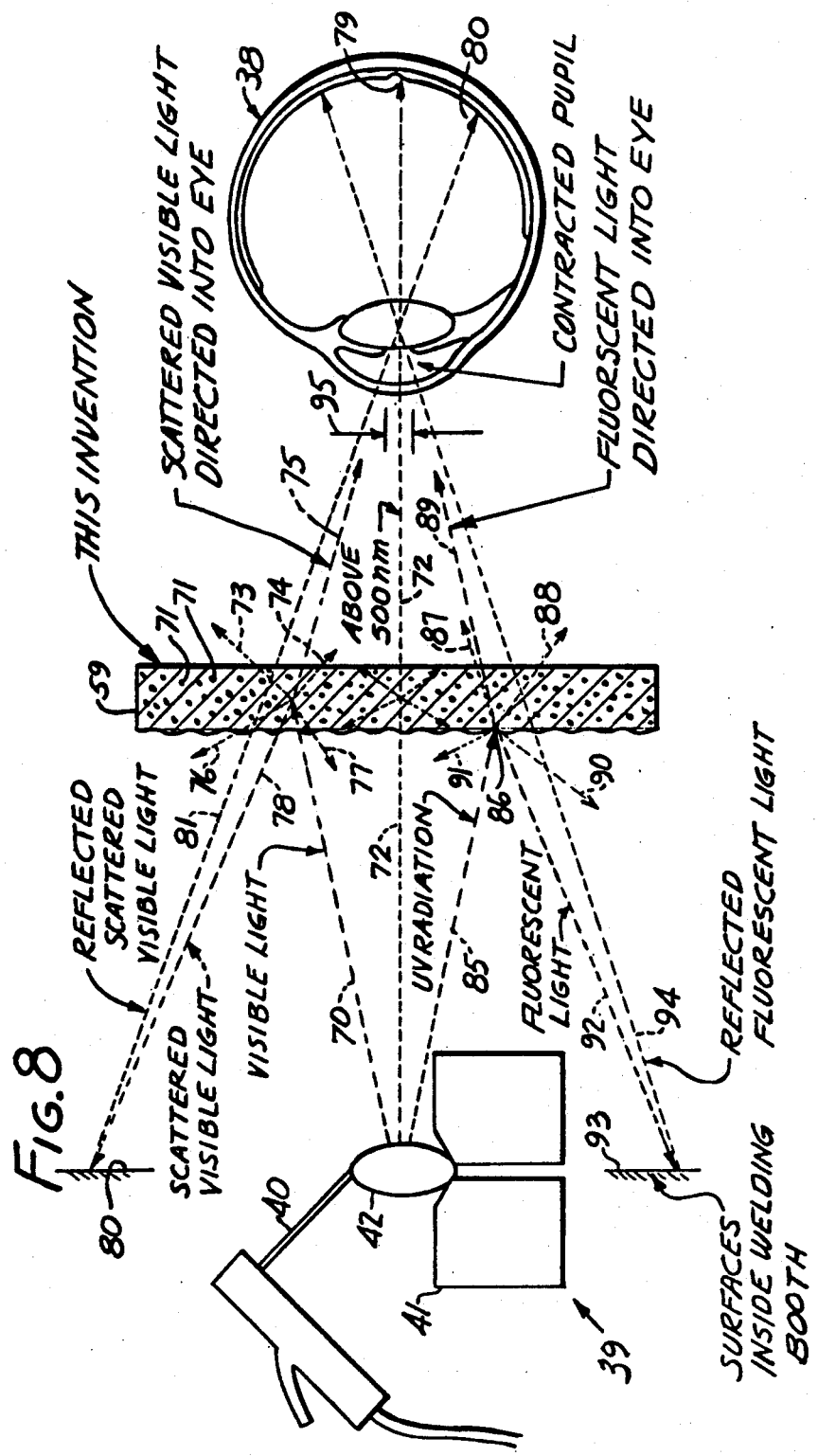

CURTAIN FOR SHROUDING WELDING OPERATIONS

CROSS REFERENCE TO OTHER APPLICATION

This is a division of applicants' copending U.S. patent application, Ser. No. 341,004, filed Jan. 20, 1982, entitled "Curtain for Shrouding Welding Operations", now U.S. Pat. No. 4,408,834 which in turn was a division of applicants' U.S. patent application Ser. No. 201,052, filed Oct. 27, 1980, entitled "Curtain for Shrouding Welding Operations", now U.S. Pat. No. 4,330,177, issued May 18, 1982, which in turn was a continuation of applicants' U.S. patent application Ser. No. 946,163, filed Sept. 27, 1978, entitled "Curtain for Shrouding Welding Operations", now abandoned.

This invention relates to welding curtains through which an object on the other side can be seen.

In welding processes, the welder is customarily protected by fire and radiation proof clothing and a helmet. It is required that he see the work he is welding, and it is customarily viewed through a very low transmission window in his helmet. The glass through which he looks is designed for this purpose.

There is another class of protection provided around welding operations, which is intended to protect persons such as adjacent workers, passers-by, and supervisors. These persons are not ordinarily as interested in the specific details of the welding operations as the welder is and therefore will customarily not look at the arc spot per se. If they desired to do so they would simply enter the enclosure and use a helmet similar to that which the welder himself utilizes. Instead, they merely want to give general supervision over the welder, or observe what he is generally doing. For example, it is desirable to assure that he has not been overcome by fumes and become helpless, or that the work is progressing satisfactorily.

For these reasons and purposes it is necessary to provide protection for the supervisor, co-worker or passer-by so that he can see through the curtain for a useful period of time and to observe what is going on behind the curtain, but he should be protected against the hazardous effects of the light of the arc.

Still, the person outside the curtain does not need the same protection as the welder, whose eyes are only a foot or so away from the arc. There are on the market at the present time numerous welding curtains for this purpose. In general each of these curtains has a rather distinctive color, and they are commonly identified by their respective color. Their stated purposes are to protect the otherwise-unprotected observer by absorbing harmful radiation. At the same time there is a competing requirement that the observer must be able to see through the curtain with reasonable clarity an object he wishes to view.

It is an object of this invention to provide a transparent welding curtain which will enable the otherwise-unprotected observer to observe a scene on the other side with the greatest clarity consistent with the requisite safety from deleterious effects, even if the eye should fixate on the arc spot for an extended period.

It is a further object of this invention to optimize the trade-off between these two competing requirements. This optimization is achieved by utilizing some or all of the following features:

I. Spectral space discrimination using dyes as described below;
II. Spatial frequency discrimination using surface refraction as described below;
III. Relative light intensity reduction by diffractive scattering, using surface or bulk index of refraction discontinuities as described below; and
IV Fluorescent wavelength shifting, using fluorescent dyes as described below.

Pertinent considerations relating to the above four features in order to decrease the hazard to the eyes while still allowing the maximum amount of visible light to penetrate the curtain are as follows:

I. SPECTRAL SPACE DISCRIMINATION

The energy emitted by an electric welding arc is given out in the form of radiant energy. Such radiant energy consists of the simultaneous emission of electromagnetic waves whose wavelengths include every wavelength from less than 200 nanometers (nm) to more than 1,400 nm. One nanometer equals one-one millionth of a millimeter in length. It is pertinent to this discussion that when these are ordered into a sequence of wavelengths, the range from 200 to 400 nm is called ultraviolet; and the range 400 to 760 nm is called visible; and the range from 760 to 1400 nm is called the infrared.

Within this whole range, only those radiations lying in the wavelength band between 400 and 760 nm elicit the response of sight, and give rise to the sensation of color when received on the retina of the eye. However, radiations anywhere in the band 200 to 1,400 nm, if their intensity is excessive, can do harm to the eye.

Among all the radiations, those of the ultraviolet (200–400 nm), and the shorter-wavelength part of the visible (400 to about 500 or 550 nm) are the most effective in producing damage to the eye. That is, the radiations whose wavelength is 500 nm and greater are relatively innocuous in causing damage even when they are present to as large an extent as the group from 200 to 500 nm. Therefore a curtain or filter which stops all radiation from an arc operation between 200 and 500 nm while allowing the residual radiations from 500 to 1,400 nm to pass, will do away with the potentially hazardous 200–500 nm radiation, while allowing the longer (500 to 1,400 nm) more innocuous radiation to pass through it. It is important to maximize the amount of the remaining non-hazardous radiations that pass through the curtain, because the ability to see the scene through the curtain depends on the amount of visible light which penetrates the curtain and reaches the eye.

There are thus two mutually contradictory requirements for a curtain which allows safe viewing of an electric welding or cutting arc scene. In order to minimize the potential eye hazard, the curtain should stop all wavelengths from 200 to 500 or 550 nm or larger. In order to maximize the ability to see the scene, the curtain should pass the maximum of those radiations which give rise to the sensation of sight—400 to 760 nm. (Radiations of wavelength longer than 760 nm are not seen by the eye). Since the shorter the wavelength the greater the potential hazard, one must determine the optimum cut-off. For purposes of this invention, the conditions encountered in the use of modern intense welding arcs (welding and cutting arcs using shielding gas and operating on 300 amperes and above) are treated.

It has been determined as described later, that if the curtain transmission cut-off is between about 500 nm and about 580 nm sufficient visible light (with wavelengths between about 500 and about 760 nm) will reach the eye, and little enough residual hazard will remain, so that such a curtain could constitute a safe and usable welding curtain for the aforementioned class of passers-by, adjacent workers, and supervisors.

A curtain made according to the principle described above, will be described by an observer as having a perceived color of "medium orange" if the cut-off wavelength is 550 nm. Similarly, a filter with a cut-off wavelength of 575 nm would be perceptively described as "deep orange", and one with a cut-off wavelength of (say) 620 nm would be perceptively described as "red".

However, the characteristic perceived sensation of "orange" light could alternatively have been evoked by a mixture of wavelengths which could include a substantial amount of radiation shorter than the 550 nm mentioned above. The use of such a mixture of wavelengths for the function of visibility would lead to hazard for the eye. Therefore, the present invention specifies the cut-off limit on wavelength as the controlling factor in decreasing hazard and maximizing visibility, and not the apparent or perceived color of the transmitted light.

II. SPATIAL FREQUENCY DISCRIMINATION

It has been pointed out that radiations from 200 to 500 nm and even larger are potentially damaging to the eye, although the hazard decreases rapidly with increasing wavelength above 500 nm. In the band 200 to 400 nm the mode of action of the potential injury is related to total amount of energy delivered to the eye. Absorbing dyes which completely stop this energy band from penetrating the curtain are available as discussed later. The mode of action of the band of energy extending from 400 to 500 nm and even larger depends primarily on the energy-density at the retina of the eye. That is, a given amount of energy in the band 400 nm—and—larger, focused on a small spot on the retina of the eye, may be a serious hazard, while if the same total amount of energy is spread out over a larger spot on the retina, it may be totally non-hazardous, even for extended longer-time viewing.

It is well-known that spreading-out of images can be carried out by defocussing the image. One such method is the wearing of spectacles with a large positive or large negative diopter measure. This is not satisfactory for the situations of present concern, because all parts of the scene will be out of focus, and an uncomfortable, nauseous feeling will come over the viewer as he views an out-of-focus scene. The present invention avoids these disadvantages by taking advantage of a peculiar feature of the electric welding arc situation. In this situation, the only feature in the scene which has such a high brightness that if it were focused on the retina could give rise to hazardous effects, is the minute arc spot itself. The remainder of the scene is of such relatively low brightness that when it is focused on the retina no hazard ensues. This invention allows one selectively to broaden the image of the minute arc spot on the retina, thus decreasing its hazard below the danger point, while leaving the diameter of the images of larger features in the scene relatively unchanged, so that sight and recognition of such features is perceived as "normal". The method of implementation is shown in the drawings and is described here.

The curtain of this invention carries on its surface minute refracting elements, (sometimes called "declivities" herein) conveniently placed there by embossing or by reticulation. Bundles of light rays from the scene pass through the surface. The declivities on the surface make only a very small angle with the surface. The declivities should preferably be oriented at random. Thus a bundle of rays from any particular point in the scene is split up into a group of sub-bundles—those which passed through adjacent but differently oriented declivities of the curtain—and are brought to a focus on the retina as a number of partially superimposed images at and surrounding the location where the original image would be were there no declivities. The image of a small arc spot will thereby be spread out on the retina to enlarge its diameter, while the image of a large feature of the scene—a finger or hand or clamp, for example, would be spread out the same absolute amount but only a negligible relative amount and so would retain its nearly normal appearance in the scene. Thus the hazard to the eye from an overly bright minute source would be negated while still retaining satisfactory visual acuity of scenes viewed through the curtain.

The net result is that the brightness of small minute features (such as an arc spot) is preferentially reduced on the retina, while the brightness and appearance of larger features of the scene is essentially unchanged.

III. RELATIVE LIGHT INTENSITY REDUCTION (SCENE CONTRAST EQUALIZATION)

The normal mechanism of the human eye in protecting itself against a too-bright potentially hazardous over-illumination is an involuntary closing of the iris of the eye, and an aversion (of the direction of sight) of the eye. Neither of these reactions is effective in the normal circumstance of electric arc-weld scene viewing for the selected class of viewers protected by this invention, i.e., adjacent workers, passers-by, and supervisors. This is because the iris responds to the total illumination on the retina, and a very small bright spot surrounded by a dim field of view, is regarded by the eye-brain system as similar to a bright star in a dark sky, that is, as a "dark" scene, and the normal response is a maintainance of a wide-open iris.

The second natural protective mechanism—the involuntary aversion of the eye direction from a bright light source—is overcome by the conscious will of the observer, be he passer-by or supervisor, to examine the scene in detail since it is normally within his work-related duty to see and to study the details of the arc-welding in the scene.

In this invention a means is provided to insure that the iris of the eye will diminish its aperture (pupil) while the arc is in operation. This is done by placing scattering centers within the body of the curtain, and/or on the surface of the curtain. Most of the light from the arc spot passes through the protective curtain in such a direction that its light would not be seen by the eye. However, a fraction (preferably about one-quarter) of this other-directed light is scattered by the curtain, and some part of the scattered light enters the eye from points of the curtain removed from the direct line of sight of the arc with respect to the eye. This scattered light from all parts of the curtain is seen by the eye, and forms a general illumination on all parts of the retina. This general illumination, in combination with the residual normal illumination of the rest of the scene, triggers the normal iris-closing response due to a general, wide-spread illumination.

The net result of the scattering feature has been a decrease in scene contrast—i.e., a reduction of bright spot intensity and a lightening of the surround, a general field-of-view illumination increase which causes the iris to contract, and a decrease in the brightness of the image of the arc spot on the retina, since some of the arc spot's brightness has been scattered away in passing through the curtain of this invention.

IV. FLUORESCENT WAVELENGTH SHIFTING

It has been pointed out that it is desirable to decrease the amount of potentially harmful short wavelength light penetrating the curtain, and to increase the amount of longer wavelength visible light so that more details of the scene may be clearly seen.

According to the invention, this objective is accomplished by incorporating a fluorescent dye material in the curtain. The characteristic feature of fluorescence is that when a ray (strictly) speaking, a quantum) of short wavelength light falls upon it, the short wavelength light may be totally absorbed and an equivalent amount of longer wavelength light will be emitted in all directions. Thus the incorporation of an appropriately selected fluorescent dye will decrease the amount of shorter wavelength light that penetrates the curtain, thereby further decreasing the hazard to the eye. Furthermore, the newly created fluorescent light, if one chooses a suitable fluor, will re-emit additional innocuous long-wavelength light, some of which will be redirected to the whole welding scene, add to the general illumination, and if the fluorescent color is chosen as will be described, will make its way unimpeded by the aforementioned sharp cut-off dye (the cut-off chosen to cooperate with the characteristic fluorescently emitted wavelength of the fluorescent dye material) through the curtain to give more visual brightness to the scene surrounding the welding arc.

A welding curtain according to this invention is preferably made utilizing an organic plastic matrix such as polyvinylchloride, which itself is opaque to certain undesirable wavelengths and which can act as a structural support and as a matrix for dyes, pigments, and additives which it may contain. One or both of its surfaces can be modified to provide the above surface refractive effects.

The above and other features of this invention will be fully understood from the following detailed description and the accompanying drawings, in which:

FIG. 4 shows a view similar to FIG. 3, but with the eye seeing through a curtain with some features of this invention;

FIG. 5 is a vignette showing the left hand surface of the curtain in FIG. 4;

FIG. 6 is a cross-section taken at line 6—6 in FIG. 5;

FIG. 7 shows the field of view and the response of an eye as it looks through a prior art curtain; and FIG. 8 shows a view similar to FIG. 7, but with the eye seeing through a curtain with some features of this invention.

Figure 1:
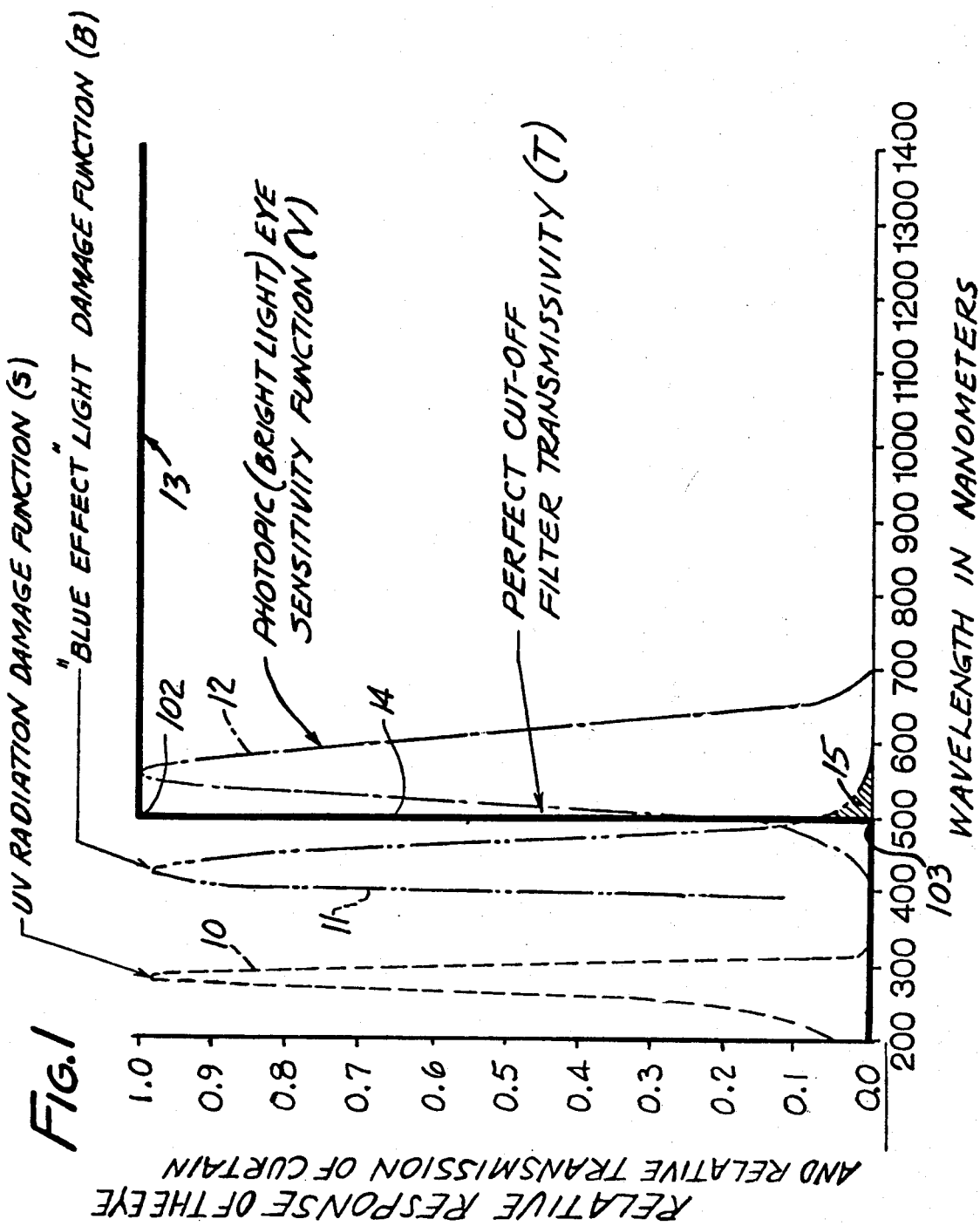
FIG. 1 is a graph showing the inter-relationship between the damage functions of ultraviolet, and of light induced retinal injury "blue effect" light damage, the transmissivity of an ideal cut-off dye, and the photopic eye sensitivity function.

FIG. 1 is a graph illustrating some of the parameters which must be considered in the use of this invention. The abscissa is the wavelength of the radiation in nanometers (nm) while the ordinate is the relative response of the eye to radiation and light and also the relative transmission of curtains at the various wavelengths. Graph line 10 shows the ultraviolet radiation damage function S. This line discloses that maximum damage is caused by radiation at about 270 nanometers. Still, however, any radiation whose value is above zero anywhere along this graph line can cause some damage. For example, at about 225 nanometers the effect is about 1/7 as important as radiation at 270 nanometers. However, it still constitutes a risk of damage from ultraviolet radiation, although a lesser risk. The use of ultraviolet absorbers in plastics to absorb the ultraviolet radiation is well-known and no claim is made to absorption of ultraviolet radiation per se. An ultraviolet absorber is conventionally used to preserve the plastic matrix, as well as to prevent transmission of ultraviolet light.

Graph line 11, shows the "blue effect"0 light hazard function (B).

This graph line shows that retinal damage begins to be caused by radiation above about 400 nm, is maximum at about 440 nm, diminishes as a hazard through 600 nm, the hazard remaining constant at one thousandth of the maximum value from 600 to 1,400 nm. The greatest risk is at about 400 nm. However, any radiation within the indicated range of sufficient intensity can cause retinal injury.

Graph line 12 is the photopic eye sensitivity function. This shows the sensitivity (V) of the eye to visible light. It rises from a zero value near 400 nm to a maximum of 555 nm and declines to near zero near 760 nm. The more of the light as weighted by this response curve which can be transmitted, the greater will be the perception to the eye of an object on the other side of the curtain.

Graph line 13 shows the transmissivity function of a theoretically perfect dye with a "cut-off" at approximately 491 nanometers. It has a rising segment 14. Especially this rising segment, and indeed the whole line, defines what the dye will absorb and not pass, and what it will not absorb and will pass. Speaking generally, points beneath and/or to the right of the curve represent transmission. Points above and/or to the left, represent absorption. The rising segment is the area of sharpest and greatest effect. A dye can be theorized the rising segment of whose curve would be at either a shorter or longer wavelength than the one shown. If it were at a shorter wavelength, it would give slightly more visible energy but would also pass a very significant additional amount of "blue effect" energy to the hazard of the viewer. Selection of a dye with a rising segment at a longer wavelength would reduce the "blue effect" light hazard, but would also diminish the amount of visible light tranmitted to the disadvantage of observer visibility. Therefore, there is no perfect dye composition, and certainly no practical dye composition, which will simultaneously entirely eliminate the "blue effect" light hazard and entirely maximize the visible transmission. Accordingly, there is a region 15 which is somewhat triangular in shape representing "blue effect" light hazard which will be transmitted even by the theoretically perfect curtain. One of the objects of this invention is to minimize the hazard to the eye of this light which unavoidably will accompany the visible light.

Figure 2:
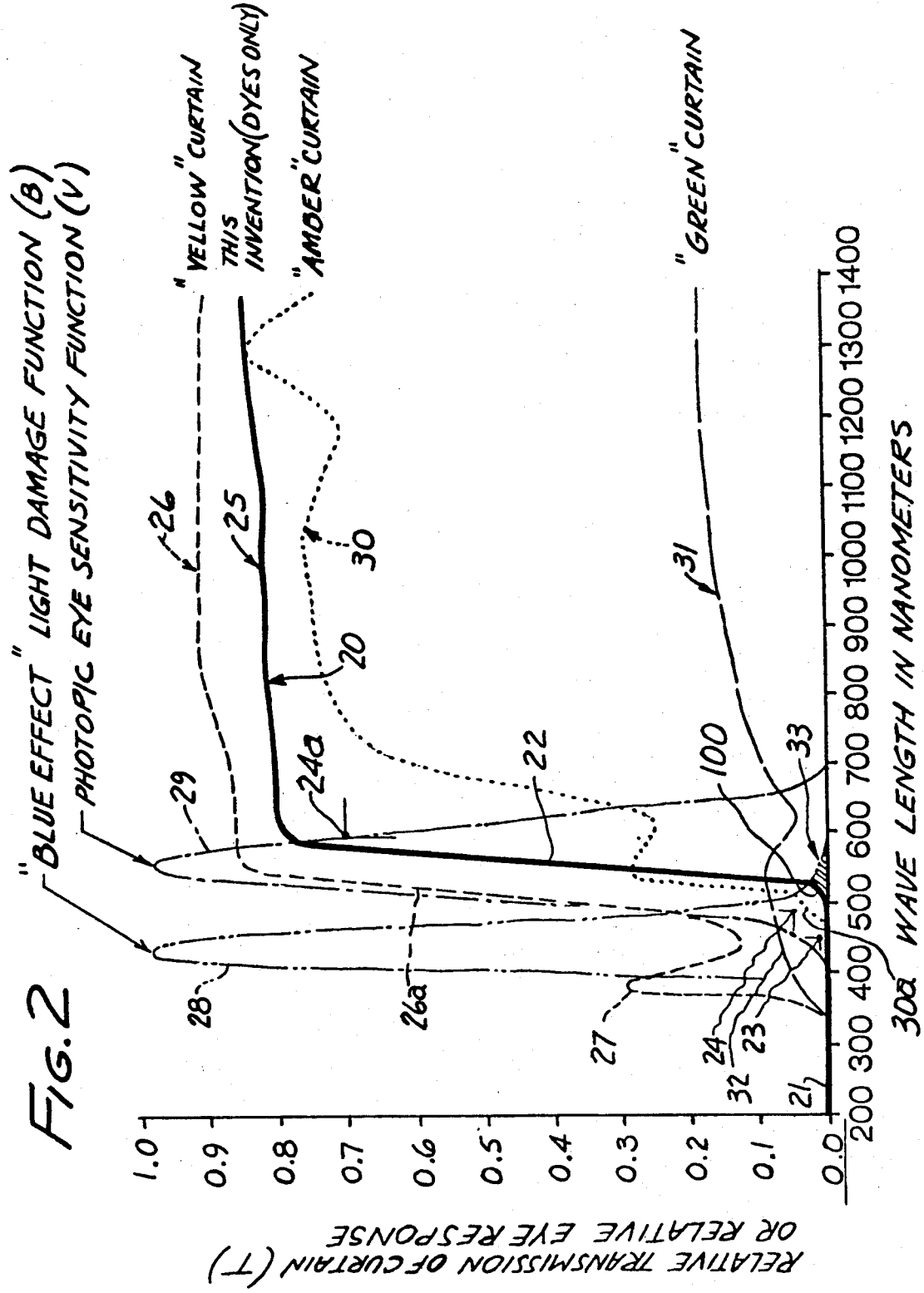
FIG. 2 is a graph showing the inter-relationship between the "blue effect" light damage function curve, the photopic curve, and the transmissivity behavior of a group of curtains.

In FIG. 2 there is shown another graph whose abscissa is wavelength in nanometers and whose ordinate is the relative transmission of the curtains (T) and relative response of the eye (B) and (V). The purpose of this graph is to contrast the performance of one representative embodiment of this invention with some prior art welding curtains. The prior art curtains described have only dyes as their active constituents for the control of light, and therefore this comparison is made without the diffracting and scattering effects of the invention being included.

Graph line 20 shows the relative transmission of a curtain with dyes only of this invention, and without the other features. It will be observed that the curve has a flat segment 21 whose ordinate value is zero between about 200 and about 500 nm, meaning that it transmits no radiation between these ranges. It then has a rising segment 22, as nearly vertical as can be devised by appropriate dye selection, from about zero transmission to about 80% transmission. Limits 23, 24 and 24A are respectively shown at 1% at 450 nm, and at 5% at 491 nm, and at 70% at 600 nm. To the right, above about 600 nanometers there is a generally flattened segment 25. This curve indicates that above about 600 nm about 75 to 85 percent of the light of various wavelengths is transmitted by the dyes, which is a very suitable value for a welding curtain.

Graph line 26 shows the relative transmission of a "yellow" dyed prior art transparent welding curtain. A substantial transmission of radiation around 390 nm is shown by a rise 27 in the line, and it will be noted that the entire rising segment 26a of the curve at cut-off is shifted to the left of rising segment 22. By "cut-off" is meant a relatively narrow wavelength range across which the transmission changes rapidly (in respect to wavelength) from a generally low value—5 to 10% to a generally high value—70 or 80%. Examples in FIG. 2 are segments 22 and 26a. Comparison of graph lines 20 and 26 with graph line 28 which shows "blue effect" light hazard and graph line 29, which is the photopic curve, shows that much more "blue effect" light is transmitted by the "yellow" curtain, although as the relative transmission curve indicates, more photopically visible light is also passed than is the case for the invention as shown by graph line 20.

Graph line 30 shows the performance of a prior art curtain often referred to as "amber" colored. It will be seen that it, too, passes more hazardous "blue effect" light, mainly attributable to segment 30a. It also has a lesser tranmission of photopically visible light than is the case for the invention herein.

Graph line 31 shows the performance of a prior art curtain often referred to as "green" colored. It will be seen that it, too, has a segment 32 to the left of segment 22 which admits "blue effect" light. It has a lesser photopically visible transmissivity than the curtain of this invention.

Region 33 is also shown which indicates the transmission by the curtain of this invention of residual "blue effect" light. The absolute effect of the residual "blue effect" light whose existence is indicated in FIG. 2 by the somewhat triangular region 33, is obtained by a mathematical weighting process. In each wavelength interval considered, (e.g. for this invention 500 to 505 nm, 505 to 510 nm, 510 to 515 nm, etc.) the value of the curtain dye transmission (T) in FIG. 2 for segments in the respective line is multiplied by the value of (B), curve 28 in FIG. 2, for the same wavelength interval, and the product multiplied by the value of the spectral radiance of an arc source with a brightness similar to the sun (L), for the same wavelength interval. The values of the final products (BLT) thus obtained for each wavelength interval are then summed. This total sum is proportional to the total "blue effect" light hazard to the eye from the residual "blue effect" light passed by the curtain under consideration. The curtain of this invention will be seen to perform in a manner which is rather close to the optimum defined by graph line 13 in FIG. 1, although it cannot be expected that any economically priced commercially available dye will be as ideal in its absorption as the theoretical dye proposed by graph line 13 of FIG. 1.

As will be discussed later, a useful method to characterize the relative rating of different curtains in safeguarding the eye and in providing adequate visibility is to compare the ratio of the total amount of visible energy transmitted by a welding curtain (VLT) with the total amount of potentially hazardous "blue effect" light energy (BLT) transmitted by the same curtain. The complete description of the method of obtaining the value of the rating factor will take into account the necessary weighing functions such as lines 11 and 12 in FIG. 1.

The spectral transmissivity of a curtain is a function of absorptive dyes in the matrix of the curtain. The "perceived" color is not to be confused with "spectral" color, even though the various curtains described do have a "color" which is perceived by the user. One refers herein to transmission and to cut-off strictly as a function of wavelength.

Assuming a suitable dye a useful curtain can be obtained, but such a curtain continues to involve the transmission of "blue effect" light to the hazard of the observer. One problem with this "blue effect" light is that the eyeball is not strongly reactive to it. The light which constitutes the "blue effect" light hazard can have wavelengths longer or shorter than that of the spectral color blue. The perceived color blue does, however, characterize the color sensed in this region. There is little pain or other sensation from it, and damage can be done because no protective action will be taken. This damage is a function of energy per unit area incident on the retina. In a welding operation, it comes from a small source to which the pupil will not be adequately reactive, but the light is strongly focused by the eye, and this increases the area loading.

This invention presents a number of ways to assist and instruct the eye for its own protection. One such technique is shown in FIG. 4, where a curtain 35 having a pair of surfaces 36, 37 is shown disposed between the eye 38 of an observer and a welding operation 39. The welding operation is indicated by schematic welding rod 40 adjacent to a workpiece 41 and generating a fireball (arc) 42 which is the source of the light being protected against herein. The lens 43 of the eye is focused on a retina 44. An iris 45 forms a variable aperture to determine the amount of light which enters the eye through an area called the pupil. More light is admitted when it is enlarged that when it is constricted. Primary rays 46, 47 are shown impinging on curtain 35 which includes a preferred feature of this invention.

Figure 3:
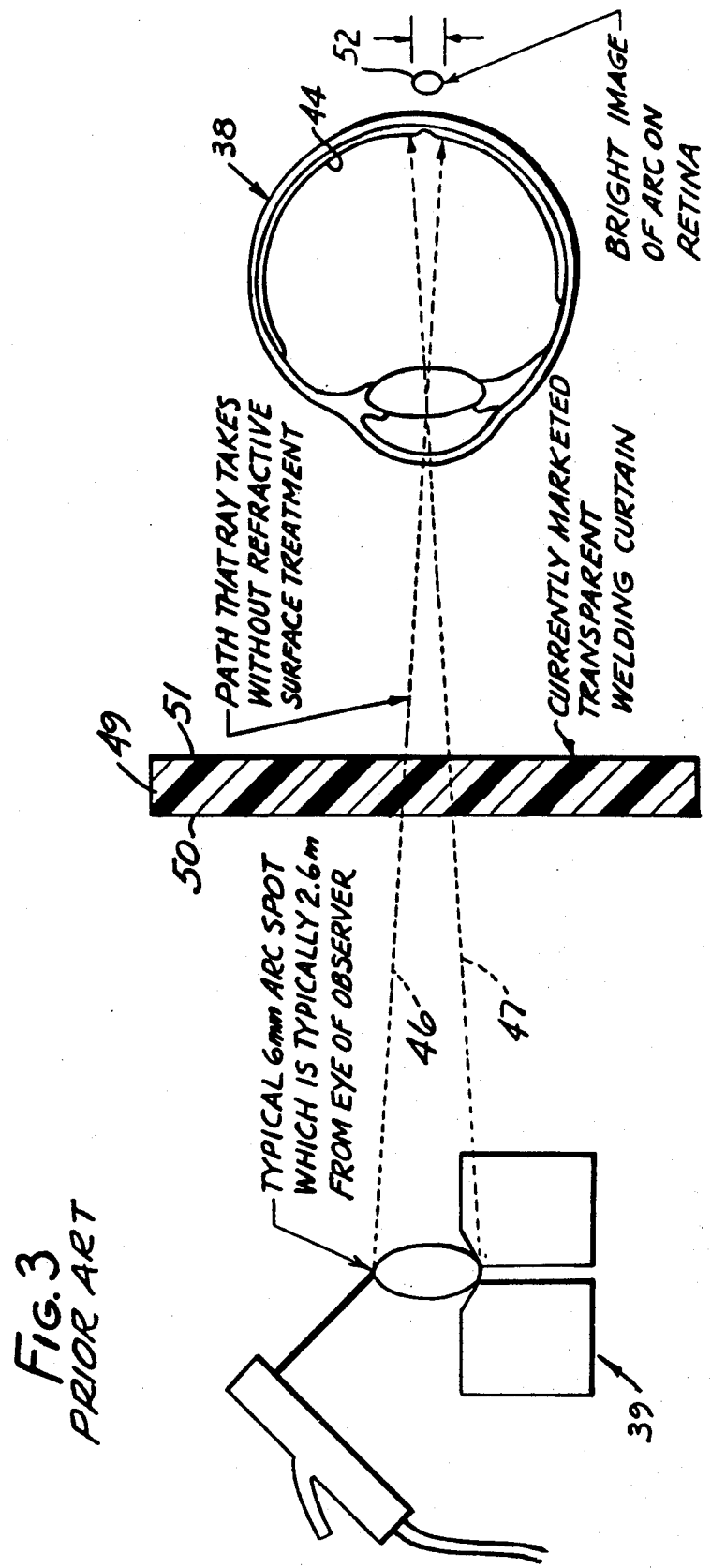
FIG. 3 shows the focusing action of the eye as it looks through a prior art curtain.

A similar view is shown in FIG. 3, where the same rays impinge on a prior art curtain 49. The prior art curtain is dyed but transparent in its color, and has two smooth parallel surfaces 50, 51. In FIG. 3, rays 46, 47 are imaged by the lens to form a central image 52 whose relative size is shown in solid oval line immediately adjacent to the retina.

In order to reduce the unit loading on the retina it is useful to spread the light as much as possible for same pupil area opening. In the preferred embodiment of the invention this is accomplished by reticulated or embossed declivities 53 on surfaces 54 as shown in FIGS. 4–6. The purpose of these variations from a planar surface is to provide surface-refractive spreading of the beam. This will spread the image and reduce the unit loading.

The best mode for forming reticulations (declivities) is by a process of reticulation. A reticulated surface can be formed by allowing the PVC plastic to pass through the last calendaring rolls at a temperature that does not fully anneal the residual crystalline moeity of the plastic sheet. When the residual stresses in the insufficiently annealed plastic are relieved the surface is distorted. Within the plastic sheet are small (a fraction of a millimeter) zones of relatively crystalline polymer. These zones act independently in regards to structural stresses. If the last calendaring roller is not hot enough to fully thermally anneal these residual stresses, they cause each separate zone to slightly contract. This contraction causes the surface to form irregularities which are known as reticulations, and are also called declivities herein. Their surfaces are, of course, non-planar.

Instead, the sheet could be embossed with adjacent or overlapping dimples or planar-bounded structures.

For purposes of disclosure, dimpled declivities are shown, and their dimensions are greatly exaggerated. For purposes of the following specific example, the size of the fireball 42 is taken to be 6 mm diameter, the distance from fireball 42 to curtain 35 or 49 is taken to be 1.3 m, and the distance from the curtain to the eye 38 of the observer, is also 1.3 m.

In general it is preferred that the tangents to the surfaces of the declivities do not exceed a difference greater than about 8 minutes of arc from parallelism with what would be smooth planar surface parallel to surface 54. This is shown by angle 54a (FIG. 6). Such an arrangement will give an image change corresponding to about a 4 minute of arc divergence on each side of the image of any object in the field of view. Such image enlargement is a considerable part of the size of the otherwise unspread arc spot image size. Indeed for the dimensions quoted the effect is to about quadruple the area on which the energy falls even though a brighter portion is still located in the center. The enlarged areas are shown as areas 55, 56, 57 58 in FIG. 4. This provides a gross enlargement in the image and spaces out the image rather in the manner of a range finder. The additional enlargement due to the 4 minutes of arc divergence on each side of a larger object of say 32 minutes of arc (a 25 mm object) will only raise the image size to that corresponding to an image appropriate to a 30 mm object—the 25 mm object would still be clearly recognizable. Even a smaller amount of spreading of the incident rays causes a substantial reduction in unit loading on the retina. The effect this surface treatment has on arc image intensity on the retina is described later. For simplification of the optical effect the declivities have been shown on one side only. Declivities with half the angle (4 minutes of arc) and of the same size on both sides of the curtain would have nearly the same effect.

The surface treatment irregularity can be provided in many ways. One way is to calendar a pattern all over the surface, and this will produce predetermined shapes, which could be defined by planes to form pyramids and the like. Instead of sharp and planar bounded declivities, these may instead be dimpled structures with curved boundaries, conveniently provided as an "orange peel" surface known to all persons accustomed to calendaring sheets of polyvinylchloride as the consequence of reticulation. Such a surface is shown in FIGS. 5 and 6, wherein the plurality of dimple-shaped concave declivities 53 are formed in the surface 54, as already described. The same criteria would apply to other types of surface irregularities, all of which are for convenience called "declivities", even though they may be convexly or concavely planar or curved in contour. It is not desirable to diffuse the image too greatly. The extent shown is optimum.

If a greater angle is chosen, the images of larger objects are spread too much to be seen. If the declivities are too large (over a few millimeter in size) the image of the arc is not divided into parts and so it can not be spread. If the declivities are too small (much less than a millimeter) they tend to scatter light instead of slightly redirecting the bundles of light. This would obscure the scene behind the curtain. Therefore the average declivity ought not to exceed about 1 mm across, and may be smaller.

Another technique to reduce the intensity of the image depends on in-body scattering, wherein at least 5% and less than 50%, and preferably about 25% of the light is likely to be scattered, and about 67% (remaining 8% is due to surface reflection) will pass through without any scattering at all to form an image. This class of scattering causes light from the arc to appear to come from the curtain itself. The curtain therefore becomes brighter, and this reduces the contrast between the background and the bright arc, while at the same time it provides illumination which causes the pupil to constrict. Materials for scattering are index of refraction discontinuities which may be particulates or voids whose index of refraction is different from that of the matrix material. The presently preferred materials are fluorescent zinc oxide, zinc oxide, and titanium dioxide, all of whose indicies of refraction are above 2.0. The index of refraction of polyvinylchloride is about 1.5. Similarly, air may be utilized, being incorporated in the matrix as bubbles. The index of refraction of air is 1.0. It is desirable for there to be a difference in index of refraction between matrix and discontinuity of at least about 0.2 for best results.

This type of scattering will cause every part of curtain 59 (FIG. 8) to scatter light into the eye 38. In FIG. 8, curtain 59 is shown with the surface treatment of curtain 35 of FIG. 4, and this is the preferred embodiment. However, the surface treatment is ignored in FIG. 8 for clarity in describing other features of the invention.

The result of the in-body scattering is that the scene perceived consists of a lower contrast (and about 25% lower arc-image intensity in the best embodiment) fireball against a relatively brighter (about four times more light appears to be emitted by the curtain itself, compared with prior art curtains without this feature) background. Such scattering centers of the type mentioned tend to preferentially scatter the wavelengths which approximate their own size. Accordingly, for the purpose of scattering wavelengths of light which pass through the curtain, particulates or other discontinuities on the order of about 500 nm in size should be utilized.

This class of scattering is shown in FIG. 8 where visible light (including the "blue effect" light) is shown as ray 70 impinging on discontinuities 71. Some of the visible light rays will of course pass directly through the curtain, but some rays will be scattered through the observer's side of the curtain as shown by scatter rays 73 and 74. Such scatter rays of course occur over the entire surface and those scattered in the direction of the eye such as ray 75 are collected by the pupil. Rays such as ray 72 may pass unscattered through the curtain directly to the eye. To the extent that scattered rays such as rays 73 and 74, and some rays which are scattered reversely such as rays 76, 77 and 78, remove energy from the beam, they cause a diminution (about 25% reduction in the preferred embodiment) in the intensity of the beam which forms the image of the arc spot on the retina of the eye. The decreased intensity of the image of the arc spot formed on the retina represents a decreased hazard from the residual "blue-effect" light component of the ray.

Those forward-scattered rays such as ray 75 that happen to be directed precisely toward the eye, will be focused on the retina at places on the retina removed from the location of the image of the arc spot 79, that is, they will be focused at about, or near 80 on the retina, and of course this is a wide-area effect from the entire surface of the curtain. Such increased brightness in all of the curtain acting as a background and projecting light to the retina over a wider area causes the iris to contract its diameter, still further diminishing the energy focused on spot 79 from the arc spot. This results in a further diminution (about 30% reduction due to iris constriction in the preferred embodiment) of the hazard from the residual "blue-effect" light component of the light from the arc spot.

Similarly rearward reflected scattered light shown by rays 76, 77 and 78 is directed into the region of the welding operation. There it may have struck some object 80, (ray 78 does this) and then have been returned as ray 81 through the curtain to the pupil, of course ray 81 may undergo some scattering itself. Rays 78 will aid in illuminating the booth, and the reflected ray 81 reaching the retina will further cause the iris to decrease its diameter with beneficial results as just described (as much as 5% reduction due to iris constriction depending on the reflective nature of object in the booth).

Still another means to protecting the eye is to provide a fluorescent dye in the curtain which is responsive to the ultraviolet radiation. Ultraviolet radiation will not pass through the curtain, but when an ultraviolet ray 85 impinges on a fluorescent dye particle 86 in the curtain, the energy of the ray will be converted to visible fluorescent light shown by rays 87-92. Forwardly, extending rays 87-89 behave in much the same manner as rays 73-75 by illuminating the curtain and making it brighter so as to instruct the eye-brain system to constrict the pupil, thereby to decrease the amount of energy which passes through the lens and onto the retina. This augments the effect of the scattering of light described above in diminishing the "blue-effect" light hazard from the focused arc spot on the retina. This effect can further reduce the apparent brightness of the arc spot by an additional 5%.

Similarly some fluorescent light will be emitted back into the work area (rays 90, 91, 92), strike an object 98 and be reflected by it as reflected ray 94 which can also reach the eye.

Dimension 95 indicates a constricted pupil caused by the constriction of the iris due to this additional light.

The fluorescent dye is responsive only when it is near (a few microns from) the surface because the ultraviolet absorber, present for another purpose, would absorb all the ultraviolet radiation that would stimulate the fluorescent dye. The fluorescent dye's response to ultraviolet stimulation is decreased with use, and as such must be continuously replenished at the surface. This is accomplished by using a mobile dye which diffuses through the body of the curtains and therefore allows fresh fluorescent dye to appear near the surface as the existing dye is exhausted.

FIG. 7 shows a prior art arrangement with a welding set-up and a conventional curtain 100 having only a dye and smooth surfaces 101, 102. It is shown passing light 103 above about 350 nm and stopping ultraviolet rays 104 and also passing visible light 105 in various directions. There is nothing to light up the curtain, so the iris remains unconstricted, as shown by dimension 107. Nothing is done to enlarge the image of the arc spot on the retina. For the same condition of relative location of arc, curtain and observer and for the same initial arc spot intensity, the potential "blue-effect" light hazard is always greater than for the curtain of this invention.

In order that persons skilled in the art may devise, evaluate, and select dyes for a welding curtain, the following discussion of how to optimize the constituents, especially the dye, will now be given. The ultimate objective is to give maximum visible transmission consistent with adequate protection against eye damage.

As has been described above, bright light sources can give rise to several different hazards to the eye. The most severe of these hazards are: (a) the ultraviolet light hazard, (b) the photochemical light-induced retinal injury, and (c) the retinal thermal injury.

The relative importance of these three modes of injury depends on the spectral distribution of the light from the source, the surface brightness of the source of light, and the time of exposure to these causative factors.

For the purpose of designing an optimum safeguard material (welding curtain) one will plan to safeguard against a luminous emitting surface which is well studied and reproducible, and which has the emissions characteristic of the most energetic welding arc situations that will be encountered. In the case of an electric welding arc, the surface brightness of the light-emitting spot does not depend on the current, because a larger value of the arc current will only increase the size of the arc spot and still leave the surface brightness unchanged. The factor which has the greatest effect on the brightness is the composition of the shielding or cutting gas. The very highest brightnesses occur in any of the following welding methods: Gas Metal Arc Welding, Gas Tungsten Arc Welding, Flux Cored Arc Welding, and Plasma Arc Cutting, when the shielding gas used in these processes contains Argon or $CO_2$. Under such circumstances the brightness (radiance) of the arc spot is between 700 and 750 watts per $cm^2$ per steradian. It is emphasized that these are the maximum radiance values under extreme conditions—that is, with the arc currents high enough to lead to magnetic constriction of the arc spot. Typical values of other welding arcs and conditions of use range down to 100 W/$cm^2$/sr. The spectra of the arcs from electric welding operations are satisfactorily approximated by a black body spectrum of 5000° K., but the radiance is less than that of a black body because the emitter is a low-pressure gas.

A suitable, reproducible and well understood representation of the arc emitter is available in the spectrum and brightness of the zenith sun as observed at the surface of the earth. Studies have shown that the brightness of the sun is 910 W/cm²/sr and that the spectrum is close to that of a black body operating at 5800° K.

In order to optimize the welding curtain it is useful and appropriate to adopt the sun's brightness and spectral distribution as a representative one, which allows a slight safety factor, for the brightness and spectral distribution of any welding arc which can be operated.

Referring now to the three most severe hazards of the electric arc light to the eye: ultraviolet, photochemical light-induced retinal injury, and retinal thermal injury, it is observed that the ultraviolet hazard is not the controlling factor. This is because additives are available (ultraviolet absorbers) which completely absorb the 200–400 nm energy band. Indeed, these materials are conventionally used to protect the curtain itself against ultraviolet deterioration and cracking.

The third-listed hazard, retinal thermal injury, depends on the rate of energy input to the eye and not upon the cumulative amount of energy delivered to the retina. In any event this hazard is overshadowed for electric arc emissions, by the "blue effect" light hazard function for the arc process. Therefore protection standards to be considered for arc processes will depend solely on controlling the second-listed factor: photochemical light-induced retinal injury, often called "blue-effect" or more commonly "blue-light" effect to emphasize that the hazard is greatest for 440 nm light but may be induced to a lesser degree by much longer wavelength light if present at great intensity. The protection standard now in informal use in the United States, and which is proposed as a protection standard, and which has been proposed as the Threshold Limit Value by the American Conference of Governmental Industrial Hygienists, is that the exposure to extended-source "blue-light" is an accumulation of 100J/cm²/sr of "blue-effect" light for exposure durations of less than 10,000 seconds. In symbols, $$\sum_{400}^{1400} L \cdot T \cdot B \cdot \Delta\lambda \leq 100 \text{ Jcm}^{-2}\text{sr}^{-1} \text{ for } t \leq 10^4 \text{ sec} \qquad \text{eq. (1)}$$

In this equation, and in other expressions here given, the symbol $$\sum_{A}^{B}$$

means the sum of all the products listed for the whole range of wavelength between a and b, $\Delta\lambda$ is the wavelength interval in which the values of L, the spectral radiance of the source, T, the spectral transmissivity of any intervening medium, and B, the "blue-effect" light hazard function are measured, $\Delta\lambda$ is the wavelength interval, and t is time in seconds.

Having described the measure of the blue-effect light hazard functions, a similar measure will be given for the visual effectiveness of a curtain for use in welding. The optimum will be a curtain which decreases the blue-effect light hazard to a value below that given by the criterion just described, while maximizing the amount of visual effectiveness of the light transmitted by the same curtain. The visual effectiveness of light penetrating the curtain can similarly be expressed as:

$$\sum_{400}^{760} L \cdot T \cdot V \cdot \Delta\lambda \qquad \text{eq. (2)}$$

where V is the photopic spectral luminous efficiency function as given in FIG. 1 (line 12), and the other symbols have the same meaning as previously given.

"Prior art" welding curtains are listed in Table I. For further information, a photographic filter is also listed. There are also listed curtains of this invention with an appropriate dye, with and without other features of the invention. For each of these curtains, the values of T, L and B were used to form the sum shown in eq. (1), and designated as $\Sigma BLT$ in Table I. The permissible time, during which the eye may fixate on the emitting spot and during which the focused energy impinges on the same spot on the retina of the eye is designated "permissible stare time"—the permissible time during which one may stare at the arc spot and still be within safety limits, in a 24 hour day. The stare time value, in seconds, is given, from eq. (1), as $$t(\text{sec}) = \frac{100 \text{ Jcm}^{-2}\text{sr}^{-1}}{\sum_{400}^{1400} L \cdot T \cdot B \cdot \Delta\lambda \ W\text{cm}^{-2}\text{sr}^{-1}}$$

The values of the stare time for each of the "prior art" curtains is given in Table I. One can evaluate the expression of eq. (2) which expresses the total amount of visible light that comes to the eye through the same curtain. The sum was evaluated for each of the curtains in the table, and the value for each is shown as $\Sigma VLT$ in Table I.

The last column in Table I shows the quotient of $\Sigma VLT/\Sigma BLT$. This quotient expresses the ratio of the visual effect produced on the observer by the visual light which penetrates the curtain, to the amount of "blue-effect" light which accompanies the visual light. Since it is desirable to have a large amount of visual light accompany the unavoidable "blue-effect" light, a large value of the ratio $\Sigma VLT/\Sigma BLT$ serves as a rating factor for a desirable curtain formulation. The higher the value of $\Sigma VLT/\Sigma BLT$, the higher the rating as a desirable curtain formulation. An optimization of the curtain would yield a curtain which passes the maximum amount of light while restricting the "blue-effect" light to a minimum value.

Referring to FIG. 1, graph line 13 shows the characteristics of a dye whose transmissivity is 0 from 200 nm to the cut-off wavelength $\lambda_c$, shown for example as 500 nm in the figure (segment 14); and whose transmissivity changes abruptly at $\lambda_c$ to 100% transmissivity from 500 to 1,400 nm.

On examining the changes in the relative values of graph lines 11 and 12 in FIG. 1 in the vicinity of the cut-off wavelength, it is clear that if the cut-off wavelength were chosen as somewhat less than 500 nm, the contribution of "blue-effect" light (line 11) would increase proportionately much more rapidly than the contribution of visible light (line 12) would decrease. Conversely, if the cut-off were chosen at slightly larger wavelengths than 500 nm, the contribution of "blue-effect" light would decrease proportionately much less than the contribution of visible light would increase.

Hence, the cut-off for a curtain dye should be chosen as far to the left in FIG. 1 as is consistent with yielding a value of $\Sigma BLT$ which, when divided into $100 J/cm^2/sr$, would result in an acceptable stare time for the use intended.

While the perfect cut-off filter (one in which the transmission changes from 0 to 100% completely at a given wavelength as in segment 14, FIG. 1) is not physically attainable, cut-off filters can be made whose transition is sufficiently sharp, and whose transition from relatively opaque to relatively transparent takes place over a narrow wavelength band. Such a class of filters is a subject of this invention, and a desirable example is shown in FIG. 2 marked "this invention" (line 20). It will be noted that the segment 22 of rapid rise is reasonably near to vertical, and that the cut-off "foot" 100 restricts the amount of "blue-effect" light, characterized by the damage function B, so that the value of the sum of BLT will be small compared to the value such sum would have for any of the "prior art" curtains whose spectra are shown in FIG. 2, and in which the "foot" is not minimized.

It was mentioned that the relative changes of $\Sigma BLT$ and $\Sigma VLT$ as a function of cut-off wavelength, and hence the value of the function $\Sigma VLT/\Sigma BLT$ is most sensitive to changes of cut-off wavelength in the vicinity of 491 nm (the values of the function B and V are equal at that wavelength, 0.21 of maximum for each).

A most desirable dye then would have its most nearly vertical segment corresponding to segment 14 in FIG. 1 displaced from 491 nm, and would have as sharp a cut-off as possible on the shorter wavelength side, marked 103 in FIG. 1. The sharp cut-off at the foot is far more important than a sharp cut-off at the high transmission end of the transition, marked 102, since for a real curtain dye the unavoidable slope of the segment corresponding to segment 14 in FIG. 1, or segment 22 in FIG. 2 has carried the long wavelength shoulder far to the right of the wavelength 491 nm. The additional contribution from B at the top cut-off wavelength is very small; the change in luminous effect depending on V is proportionally not great.

The consequence of this analysis is that the most useful dyes for the curtains under consideration must have a steep rise (compare segment 14 in FIG. 1), a sharp foot (compare foot 100 in FIG. 2), and the steep rise should take place at a wavelength removed from 491 nm. The last part of the requirement comes about since because the sensitivity of the ratio $\Sigma VLT/\Sigma BLT$ is greatest at 491 nm, relatively slight changes in the concentration of the dye in the curtain, and hence in the transmissivity, will shift the value of $\Sigma VLT/\Sigma BLT$ unacceptably due to unavoidable manufacturing process variations.

A description of a dye for optimum curtain manufacture is best done by specifying design points in the curve of FIG. 2.

The transmission vs wavelength curve (FIGS. 1 and 2) should have limits as follows:

Limit 23: at 450 nm, the relative transmission should not be greater than 0.01 (1%).

Limit 24: at 491 nm, the relative transmission should not be greater than 0.05 (5%).

Limit 24a: at 600 nm, the relative transmission should be at least (70%).

This relates only to an organic plastic matrix with dye, with smooth surfaces, and without any scattering function. These additional functions will improve the curtain even without the optimum dyes. FIGS. 1 and 2 illustrate only the dye's function.

Control and variation of permissible stare time is accomplished by means of the following procedures.

I. SPECTRAL SPACE DISCRIMINATION

The dye composition and concentration is varied so that the segment corresponding to line 14 in FIG. 1 is displaced sensibly parallel to itself, but to the right or left.

II. SPATIAL FREQUENCY DISTRIBUTION

Surface refraction is used to preferentially reduce the brightness of the image of the small arc spot on the retina, and therefore decrease the sum $\Sigma BLT$ on the retina, while leaving the intensity of large features of the scene sensibly unchanged.

III. FEATURES OF SCENE CONTRAST EQUALIZATION

Surface and volume scattering reduce the value of BLT and VLT, and cause the curtain to scatter light to the general field of view. This causes the iris to contract and diminishes the size of the pupil of the eye, and so the energy delivered to the retina at the image location of the arc spot is further diminished.

IV. FEATURES OF FLUORESCENT WAVELENGTH SHIFTING

This will add to the illumination of the scene, further reducing the size of the pupil, hence the energy delivered to the retina at the image location of the arc spot is further diminished. On the other hand, the value of $\Sigma VLT$ will be increased because some of the fluorescent light falls on the scene and increases the general visible-light level by which features of the scene are seen. This last factor can offset some or all of the loss of $\Sigma VLT$ caused by scattering discussed in III directly above, but it does not change the effect of III in diminishing $\Sigma BLT$.

RESULTS FROM TEST CURTAINS MADE ACCORDING TO THE PRINCIPLES OF THIS INVENTION

There have been made and tested welding curtains made using the methods designated I, II, III and IV above. These methods were used in different curtains singly and in various combinations. One of the new curtains used method I only, (i.e., a dye only in a plastic matrix which contained an ultraviolet absorber) with no additives or processes to give contributions from methods II, III, or IV. The results are shown in Table I, marked "this invention, cut-off dye only". Even though this was the least effective of the new curtains, it surpassed all "prior art" curtains by a considerable margin with a large rating factor, a smaller $\Sigma BLT$ and hence a longer permissible stare time than any of the prior art curtains.

When curtains were made and tested which used all of the features marked I, II, III, and IV simultaneously results as shown in Table I marked "This Invention With Cut-Off Dye, Refracting Surfaces, scattering particles, and Fluorescent Dye" were obtained. In the evaluations of $\Sigma BLT$ and $\Sigma VLT$ for the curtain incorporating all features I, II, III and IV no allowance was made for the additional safety effect that should be ascribed to the closing of the iris and the diminution of the size of the pupil. The value of the additional safety due to the closing of the iris because of the use of these features, depends on the level of ambient lighting in the vicinity of the welding booth, which is a level that cannot be predicted by the manufacturer of curtains. It is better practice to leave this additional uncounted diminution of ΣBLT as an additional safety factor, which is in the range of 1.5 for the conditions of ambient lighting found in typical welding fabrication shops.

The said four features are useful, applied singly to a curtain, or in any combination of one or more. For example, any or all of: surface diffraction, in-body or surface scattering, and fluorescence would improve the function of the prior art curtains shown in FIG. 2. The presence of a dye according to this invention is not essential to the usage of the other features. Suitable features can be selected for the result desired.

In Table II there is shown a list of materials of construction with which it is possible to make the best mode curtain, and also to make curtains of lesser but still adequate performance, and to make some advantages of the invention available even in curtains having dyes which do not function according to the criteria of this invention.

In describing the dyes, considerable difficulty is encountered, because their compositions tend to be regarded by their manufacturers as trade secrets. In general, metallic azo dyes, a wellknown type of dye, are preferred for their stability. Curtains with such dyes should last a considerable time without undue fading, because metallic azo dyes are quite resistant to fading. However, any type of dye with a suitable cut-off in accordance with meeting the criteria of this invention, can be used instead of the exemplary dyes disclosed herein.

Most fluorescent dyes are not as stable as the metallic azo dyes. It is possible to use only a fluorescent dye, and not use any other dye. The curtain could then be expected to fade sooner. In the best mode curtain, both a metallic azo dye and a fluorescent dye will be used.

As to the scattering materials, their size is selected to approximate the wavelength preferentially to be scattered. The most appropriate materials are any of the following: air bubbles, zinc oxide powder, fluorescent zinc oxide powder, titanium dioxide powder, or mixtures of them. Fluorescent zinc oxide performs a dual function of both scattering and fluorescing.

The fire retardant is selected in addition to its major function, for having an optical index of refraction nearly equal to that of the base polymer. Then the mixture is as transparent as the matrix.

The organic plastic matrix is preferably polyvinylchloride. It works well, is well-understood, and has a suitable life. Of course other transparent organic plastic materials could be used instead. Polyvinylchloride is given merely as an example of a large number of suitable materials.

The plasticizers will be those known in the art for use with the selected matrix material.

Ultraviolet absorbers are well-known, and need no detailed description here.

| BEST MODE CURTAIN (with reference to Table II). Percentages are by weight and are approximate: | |
|---|---|
| The identified "Base Polymer" | 41% |
| DOP plasticizer | 41% |
| The metallic azo dye identified as Sc-39-3 s/s bright orange | 1¼% |
| The fluorescent orange dye identified as C507XX Product No. 40-26-2 | ¼% |
| The identified fluorescent zinc oxide phosphor, particle size about 500 nm | 0.17% |
| The identified UV absorber | 1% |
| The identified fire retardant | 15% |

This curtain will be provided with declivities on both of its surfaces, produced by reticulation.

OTHER CURTAINS

1. The "2nd choice" fluorescent orange dye may be substituted for the fluorescent dye in the best mode curtain.
2. The "2nd choice" pigment (titanium dioxide), zinc oxide, or air bubbles of the same size, may be substituted for the fluorescent zinc oxide.
3. Dioctyl azelate may be substituted for the DOP plasticizer.
4. The "2nd choice" metallic azo dye may be substituted for the first choice dye.
5. The curtains with different dyes, the scattering materials, or surface treatment, or both, can be provided.

TABLE I

| Curtain | BLT | VLT | Permissible Stare Time | Rating Factor VLT BLT |
|---|---|---|---|---|
| This Invention With Cut-off Dye, Refracting Surfaces, Scattering Particles, and Fluorescent Dye | 0.12 | 39.4 | 833 sec (13.9 min.) | 328 |
| "Orange" Photographic Filter (Wratten 22) | 0.32 | 71.5 | 312 sec. (5.2 min.) | 223 |
| This Invention, Cut-Off Dye only | 0.32 | 52.5 | 312 sec. (5.2 min.) | 164 |
| Prior Art "Amber" | 0.50 | 34.0 | 200 sec. (3.3 min.) | 68 |
| Prior Art "Yellow" | 16.5 | 127.0 | 6 sec. | 8 |
| Prior Art "Gray" | 2.7 | 8.7 | 37 sec. | 3.2 |
| Prior Art "Green" | 5.3 | 12.9 | 19 sec. | 2.4 |
| Prior Art "Blue" | 59.1 | 41.3 | 1.7 sec. | 0.70 |

TABLE II

| | MATERIALS OF CONSTRUCTION | | | |
|---|---|---|---|---|
| PURPOSE OF COMPONENT MATERIAL IN CURTAIN | GENERAL NAME | MANUFACTURERS PART NUMBER | AMOUNT USED IN CURTAIN % WT. | MANUFACTURERS NAME AND LOCATION |
| Base Polymer | Poly Vinyl Cloride (PVC) | PVC POLYMER | 75 to 35% typically 41% | Conoco Chemicals Div. of Continental Oil Co. Houston, Texas |
| Plasticizer | Dioctyl Phthalate (D.O.P.) [Di-2-Ethyl-hexyl phtha- | DOP Plasticizer | 25 to 50% typically 41% | Mobay Chemical Corp. Pittsburg, Pa. |

TABLE II-continued
MATERIALS OF CONSTRUCTION

| PURPOSE OF COMPONENT MATERIAL IN CURTAIN | GENERAL NAME | MANUFACTURERS PART NUMBER | AMOUNT USED IN CURTAIN % WT. | MANUFACTURERS NAME AND LOCATION |
|---|---|---|---|---|
| | late] | | | |
| Orange Dye with cut-off at 540 nm and high light stability | Metallic Azo | Sc-39-3 s/s Bright Orange | ¼ to 1½% typically 1½% | 7-K Color Corp. Hollywood, Ca. |
| Fluorescent orange dye with cut-off at 540 nm stimulated by 300 nm to 400 nm emits at 420 nm to 600 nm with peak at 550 nm | Heterocyclic oil soluble mobile | C507XX Product No. 40-26-2 | ¼ to 1% typically ½% | Shannon Luminous Materials Inc. Hollywood, Ca. |
| Light scattering Fluorescent Pigment 0.5 to 2 micrion Dia. stimulated by 250 nm to 400 nm emits at 500 nm | Fluorescent Zinc Oxide Phosphor | Ottalume 2100 M | 0.05 to 0.5% typically 0.17% | Ottawa Chemical Div. of Ferro Corporation Toledo, Ohio. |
| UV Absorber | 2-Hydroxy-4-N—Octoxybenzo-phenone | UV-Chek AM300 | ¼ to 1% typically 1% | Ferro Ottawa Corp. Toledo, Ohio. |
| Fire Retardant Index of Refraction 1.5 | Barium Meta Borate Pigment | Busan 11-Ml | 10 to 20% typically 15% | Buckman Laboratories Inc. Memphis, Tenn. |
| Orange Dye with cut-off at 540 nm, and high light stability (2nd choice) | Metallic Azo | Pylam Orange 727782 | ¼ to 1½% typically 1½% | Pylam Products Company, Inc. Queens Village, New York 926-446 Ingham |
| Fluorescent Orange Dye with cut-off at 540 nm, stimulated by 300 nm to 400 nm and emits at 420 nm to 600 nm with peak at 550 nm (2nd choice) | Alcohol Soluble | C507 x 40-25-3 | ¼ to 1% typically ½% | Shannon Luminous Materials Inc. Hollywood, Ca. |
| Light Scattering Pigment 0.5 to 2 Micron Dia (2nd choice) | Titanium Dioxide | RF-3 | 0.05 to 0.5% typically 0.17% | New Jersey Zinc Company Bethlehem, Pennsylvania |
| Plasticizer (2nd choice) | Dioctyl Azelate (DOZ) | Plastolein 9058 DOZ | 25–50% typically 41% | Emery Industries Cincinnati, Ohio |

This invention thereby provides advantages useful in prior art type curtains, and also provides an entirely new concept and curtain to protect persons from welding light while permitting them to observe the scene. The invention optimizes visibility relative to hazard, and also reduces the hazard. It thereby enables adequate supervision to be maintained over the events in the welding booth.

This invention is not to be limited by the embodiments shown in the drawings and described in the description, which are given by way of example and not of limitation, but only in accordance with the scope of the appended claims.

We claim:

1. In a welding curtain of substantial area forming at least a portion of the perimeter of an area in which an electrical arc welding or an electrical arc cutting operation is conducted for the purpose of protecting the eyes of an observer located outside of said perimeter from damage by light from said arcs, said curtain having a pair of surfaces spaced apart by a dimension of thickness, and being sufficiently clear for said observer to see through it can object of substantial size located inside said perimeter, the improvement comprising: one of said surface being covered with declivities having faces disposed at angles to the plane of the sheet, whereby some rays of light, which pass through said one surface are refracted and undergo a change in direction.

2. A curtain according to claim 1 in which said angles are less than about eight minutes of arc.

3. A curtain according to claim 1 in which the declivities have non-planar surfaces.

4. A curtain according to claim 3 in which the declivities are formed by reticulation.

5. A curtain according to claim 1 in which said declivities are formed on both surfaces of the curtain, the said angles being less than about four minutes of arc.

* * * * *